(12) United States Patent
Govindan Radhakrishnan et al.

(10) Patent No.: US 11,833,276 B2
(45) Date of Patent: Dec. 5, 2023

(54) VOLATILE COMPOSITION DISPENSER

(71) Applicant: The Procter & Gamble Company, Cincinnati, OH (US)

(72) Inventors: Kumaresh Govindan Radhakrishnan, Singapore (SG); Rahul Vyas, Singapore (SG); Thinh Nguyen Ha, Cincinnati, OH (US); Stefano Deflorian, Trento (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/079,918

(22) Filed: Dec. 13, 2022

(65) Prior Publication Data

US 2023/0107386 A1  Apr. 6, 2023

Related U.S. Application Data

(62) Division of application No. 16/558,370, filed on Sep. 3, 2019, now Pat. No. 11,554,192.

(60) Provisional application No. 62/728,073, filed on Sep. 7, 2018.

(51) Int. Cl.
*A61L 9/12* (2006.01)

(52) U.S. Cl.
CPC ........... *A61L 9/12* (2013.01); *A61L 2209/131* (2013.01)

(58) Field of Classification Search
CPC .......................... A61L 9/12; A61L 2209/131
USPC ........................ 239/6, 34, 57, 145
See application file for complete search history.

(56) References Cited

U.S. PATENT DOCUMENTS

| | | |
|---|---|---|
| 10,143,766 B2 | 12/2018 | Gruenbacher |
| 2008/0194743 A1 | 8/2008 | Rotzinger et al. |
| 2011/0072711 A1 | 3/2011 | Black et al. |
| 2014/0209698 A1 | 7/2014 | Olchovy et al. |
| 2015/0027855 A1 | 1/2015 | Dabek et al. |
| 2016/0168518 A1 | 6/2016 | Roselle |
| 2017/0043047 A1 | 2/2017 | Beck |
| 2017/0151322 A9 | 6/2017 | Karpilow et al. |
| 2017/0319731 A1 | 11/2017 | Hasenoehrl |
| 2017/0319732 A1 | 11/2017 | Hasenoehrl |
| 2017/0319733 A1 | 11/2017 | Hu |

(Continued)

FOREIGN PATENT DOCUMENTS

| | | |
|---|---|---|
| CN | 101141983 A | 3/2008 |
| CN | 104321042 A | 1/2015 |

(Continued)

OTHER PUBLICATIONS

PCT Search Report and Written Opinion for PCT/USUS2019/045053 dated Feb. 10, 2020, 24 pages.

(Continued)

*Primary Examiner* — Christopher S Kim
(74) *Attorney, Agent, or Firm* — Carolyn S. Powell

(57) ABSTRACT

A method of manufacturing a volatile composition dispenser is disclosed. A container is positioned on a pallet, wherein the container has a bottom wall and side walls extending circumferentially around the bottom wall to define a reservoir and wherein the side walls have a circumferential inner edge defining a reservoir opening. The pallet is moved to a filling station in fluid communication with a tank containing a perfume composition. The perfume composition is dispensed into the exposed reservoir. A vapor impermeable substrate is attached to the planar surface of the container containing the dispensed perfume composition.

17 Claims, 7 Drawing Sheets

(56) References Cited

U.S. PATENT DOCUMENTS

| | | |
|---|---|---|
| 2017/0319734 A1 | 11/2017 | Deflorian |
| 2018/0312315 A1 | 11/2018 | Beck |
| 2019/0134245 A1 | 5/2019 | Vyas |
| 2020/0078486 A1 | 3/2020 | Govindan Radhakrishnan |

FOREIGN PATENT DOCUMENTS

| | | |
|---|---|---|
| CN | 107847628 A | 3/2018 |
| EP | 0098916 A2 | 1/1984 |
| EP | 1518794 A1 | 3/2005 |
| JP | H069659 Y2 | 3/1994 |
| JP | 2004057002 A | 2/2004 |
| JP | 2004067689 A | 3/2004 |
| JP | 2004535223 A | 11/2004 |
| JP | 2005261805 A | 9/2005 |
| JP | 2015502787 A | 1/2015 |
| JP | 2015525093 A | 9/2015 |
| JP | 2015181103 A | 10/2015 |
| JP | 2017038942 A | 2/2017 |
| JP | 2017065767 A | 4/2017 |
| JP | 2017515761 A | 6/2017 |
| TW | M301060 U | 11/2006 |
| WO | 2013076033 A1 | 5/2013 |
| WO | 2013176925 A1 | 11/2013 |
| WO | 2015181103 A1 | 12/2015 |
| WO | 2016199084 A1 | 12/2016 |
| WO | 2017151322 A1 | 9/2017 |

OTHER PUBLICATIONS

All Office Actions; U.S. Appl. No. 16/558,370, filed Sep. 3, 2019.

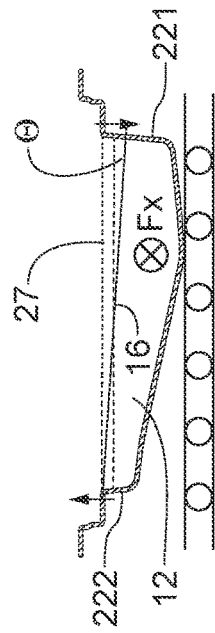
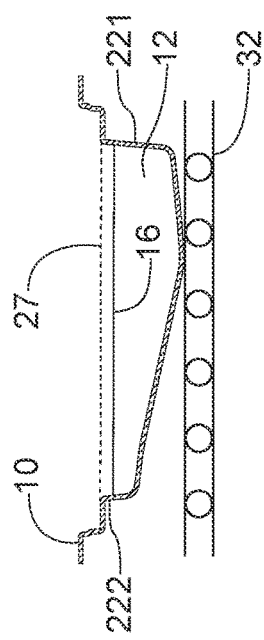
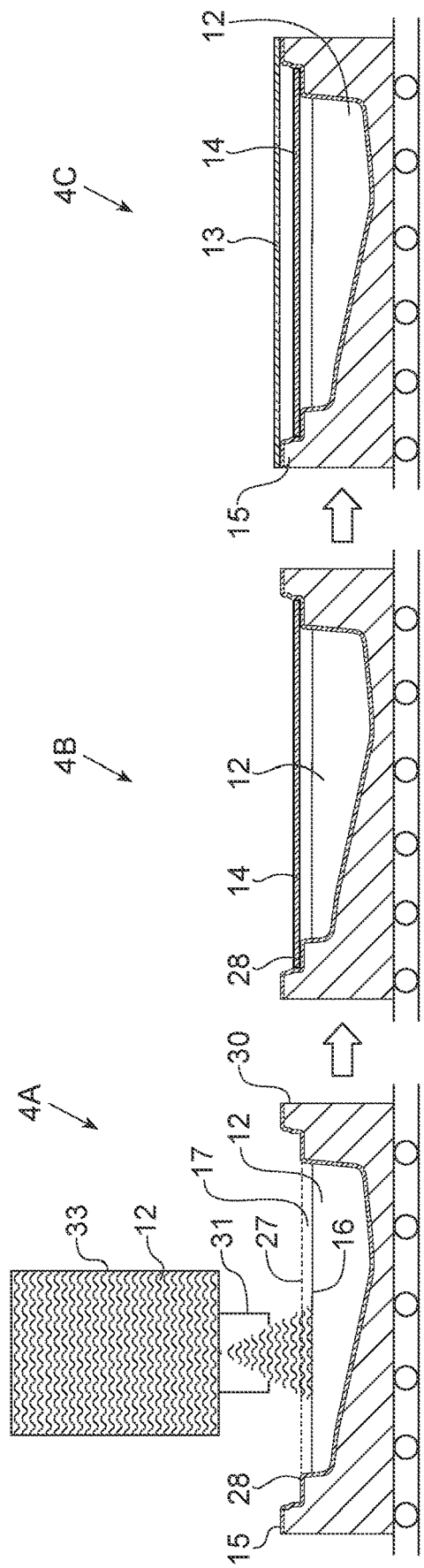

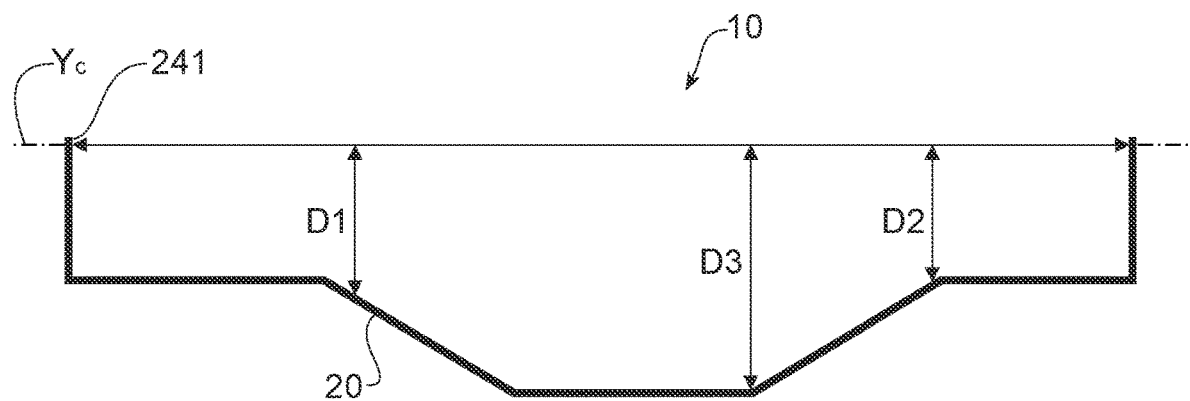
FIG. 6
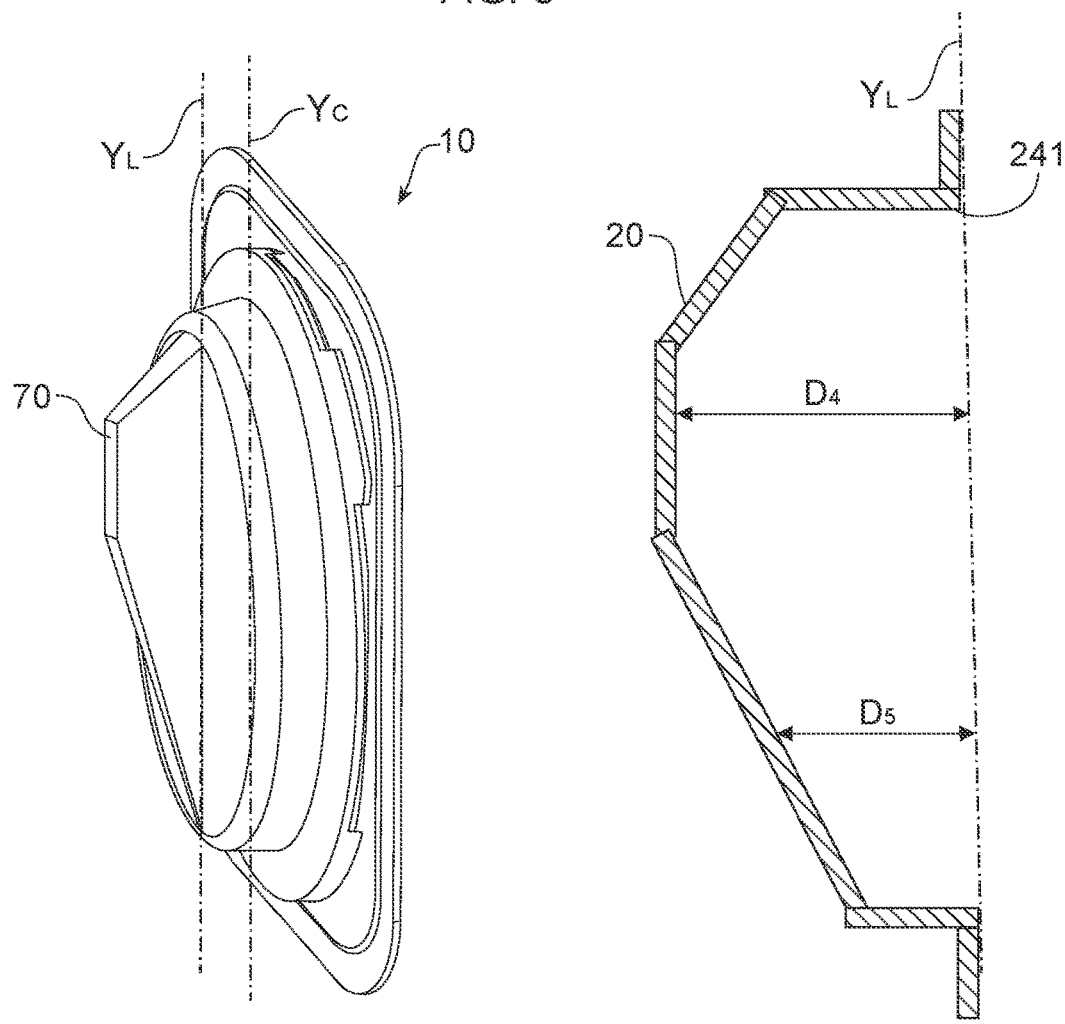
FIG. 7A
FIG. 7B

VOLATILE COMPOSITION DISPENSER

FIELD OF THE INVENTION

The invention relates to a volatile composition dispenser and methods of making the same.

BACKGROUND OF THE INVENTION

A conventional liquid air freshener has a liquid perfume delivery engine housed in a housing wherein the housing has one or more apertures for delivering air freshening benefits. The perfume delivery engine is made up of a container containing a liquid perfume, a foil sealably attached to the container to prevent diffusion of vapor phase from the perfume from the container before use and a membrane arranged within the container for allowing vaporization of the perfume after the foil is ruptured or removed. To manufacture the delivery engine, the container is filled with the liquid perfume and sealed with the foil.

However, when the containers containing the liquid perfume are shaken or caused to shake during manufacturing prior to a process of sealing the container containing perfume with the foil, the movement causes movement of the perfume in the containers which may result in perfume splashed onto surfaces in the container designed for subsequent secondary process steps such as for example, attaching of the foil or further to the container. Still further, the perfume may also splash onto the membrane thereby resulting in scrapping of such delivery engines with membranes with the perfume splash prior to use.

Accordingly, there is a need to have a volatile composition dispenser with improved manufacturability and a method for sequentially filling perfume in a container for a perfume delivery engine at an increased production rate minimizing perfume splash.

BRIEF DESCRIPTION OF THE DRAWINGS

FIGS. 3A and 3B are schematic diagrams showing the perfume composition in the container of FIG. 2A before and after subjected to horizontal acceleration in a method of manufacturing a volatile composition dispenser according to the present invention;

FIGS. 4A, 4B and 4C are schematic diagrams showing steps of a method of manufacturing a volatile composition dispenser according to the present invention;

FIG. 6 is a side section view of a variation of a container of a volatile composition dispenser according to the present invention in a horizontal orientation when placed on a support;

FIG. 7A is a perspective view of a variation of a container of a volatile composition dispenser according to the present invention in a vertical orientation when placed on a support;

FIG. 7B is a side cross section of the container of FIG. 7A;

DETAILED DESCRIPTION OF THE INVENTION

Figure 1:
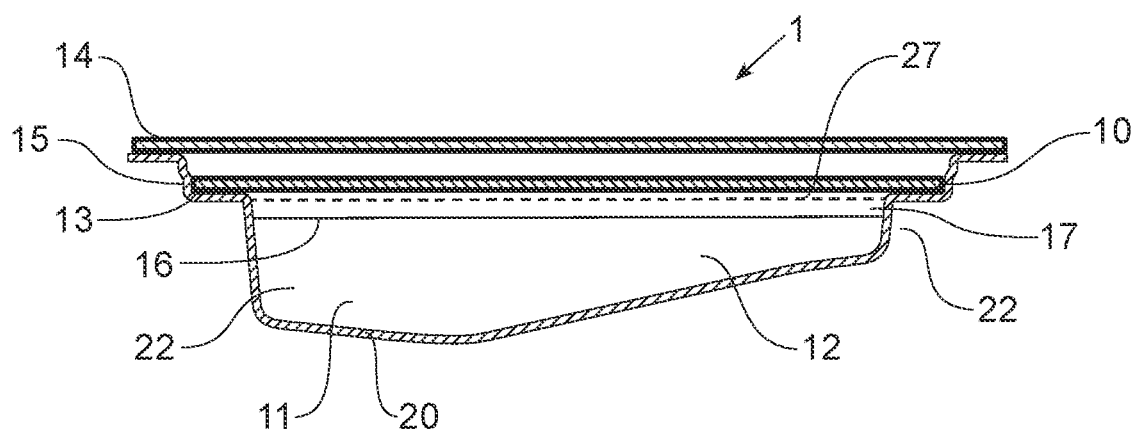
FIG. 1 is a side cross section view of a volatile composition dispenser according to the present invention in a horizontal orientation when the dispenser is placed on a support.

The present invention relates to a volatile composition dispenser (hereinafter "dispenser") with splash control design features and method of manufacturing a volatile composition dispenser. Specifically, the dispenser comprises a reservoir for receiving a perfume composition. The dispenser comprises a container having a bottom wall and side walls extending from the bottom wall to create the reservoir. The side walls have a circumferential inner edge defining a reservoir opening and a reservoir opening plane extends across the reservoir opening and intersects the circumferential inner edge. The reservoir opening plane has a center longitudinal axis extending along a length of the reservoir opening plane between opposing circumferential inner edges and extending through a centroid of the reservoir opening plane. A first depth (D1) and a second depth (D2) between the bottom wall and the reservoir opening plane is measured orthogonal to the longitudinal axis. D1 is measured ⅕ of the length from a first circumferential inner edge and D2 is measured ⅘ of the length from the first circumferential inner edge. D1 is longer than D2 to define an asymmetric profile of the bottom wall, thereby enabling control of perfume splash from the reservoir during transport of the container in the method of manufacturing the dispenser.

In the following description, the dispenser described is a consumer product, such as an air freshener, for evaporating a perfume composition in spaces to deliver a variety of benefits such as freshening, malodor removal or scenting of air in spaces such as rooms in household and commercial establishments, or enclosed spaces such as a vehicle passenger compartment space. However, it is contemplated that the dispenser may be configured for use in a variety of applications to deliver volatile materials to the atmosphere and the dispenser may include but is not limited to consumer products, such as, for example air freshening products. Further, the container described has a reservoir opening having a substantially elliptical shape. However, it is contemplated that the container may be configured in a variety of geometrical shapes including but not limited to squares, rectangles, polygons, circles, or the like.

Prior to describing the present invention in detail, the following terms are defined for clarity. Terms not defined should be given their ordinary meaning as understood by a skilled person in the relevant art.

"Horizontal orientation" as used herein, refers to a position of a volatile composition dispenser according to the present invention wherein the membrane is facing the environment in an upward or downward position.

"Membrane" as used herein, refers to a semi-permeable material which allows some components of matter to pass through but stops other components. Of the components that pass through, the membrane moderates the permeation of components i.e. some components permeate faster than other components. Such components may include molecules, ions or particles.

"Microporous membrane" as used herein, refers to a material having a network of pores.

"Vertical orientation" as used herein, refers to a position of a volatile composition dispenser according to the present invention wherein the membrane is facing the environment in a forward facing position or in a rear facing position.

FIG. 1 is a side section view of a volatile composition dispenser 1 (hereinafter "dispenser") according to the present invention in a horizontal orientation when the dispenser 1 is placed on a support. The dispenser 1 can be constructed as a disposable, single-use item or one that it is replenished with a volatile composition including but limited to a perfume composition. The dispenser 1 comprises a container 10 having a bottom wall 20 and side walls 22 extending circumferentially around the bottom wall 20 to define a reservoir 11 for containing a perfume composition 12.

The container 10 may be made of a substantially vapor impermeable material designed to resist diffusion of a vapor phase of the volatile composition 12. For example, the container 10 may be made of metal, glass, ceramic, porcelain, tile and plastic including but not limited to thermoplastics and other known materials suitable for thermoforming, injection molding and blow molding.

A membrane 13 may be disposed within the container 10 and arranged to be in fluid communication with the perfume composition 12. The dispenser 1 may further include a vapor impermeable substrate 14 adjacent to the membrane 13 wherein the vapor impermeable substrate 14 is configured to prevent release of the perfume composition 12 before use.

Figure 10:
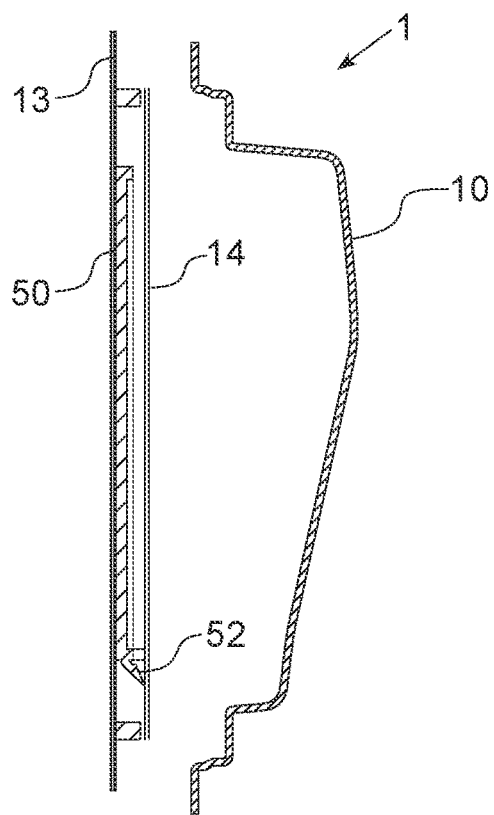
FIG. 10 is a side section view of components of a variation of a volatile composition dispenser according to the present invention.

Referring to FIG. 1, the vapor impermeable substrate 14 may be releasably attached to an outer periphery 15 of the container 10 to form a removeable cover for the dispenser 1. The vapor impermeable substrate 14 may be rupturable to allow the perfume composition 12 to pass through when ruptured. For example, as shown in FIG. 4C, FIG. 10, the vapor impermeable substrate 14 may be a rupturable substrate disposed adjacent to the membrane 13 and attached to an inner periphery of the container 10 to form a sealed perfume reservoir adjacent the membrane 13.

Figure 2B:
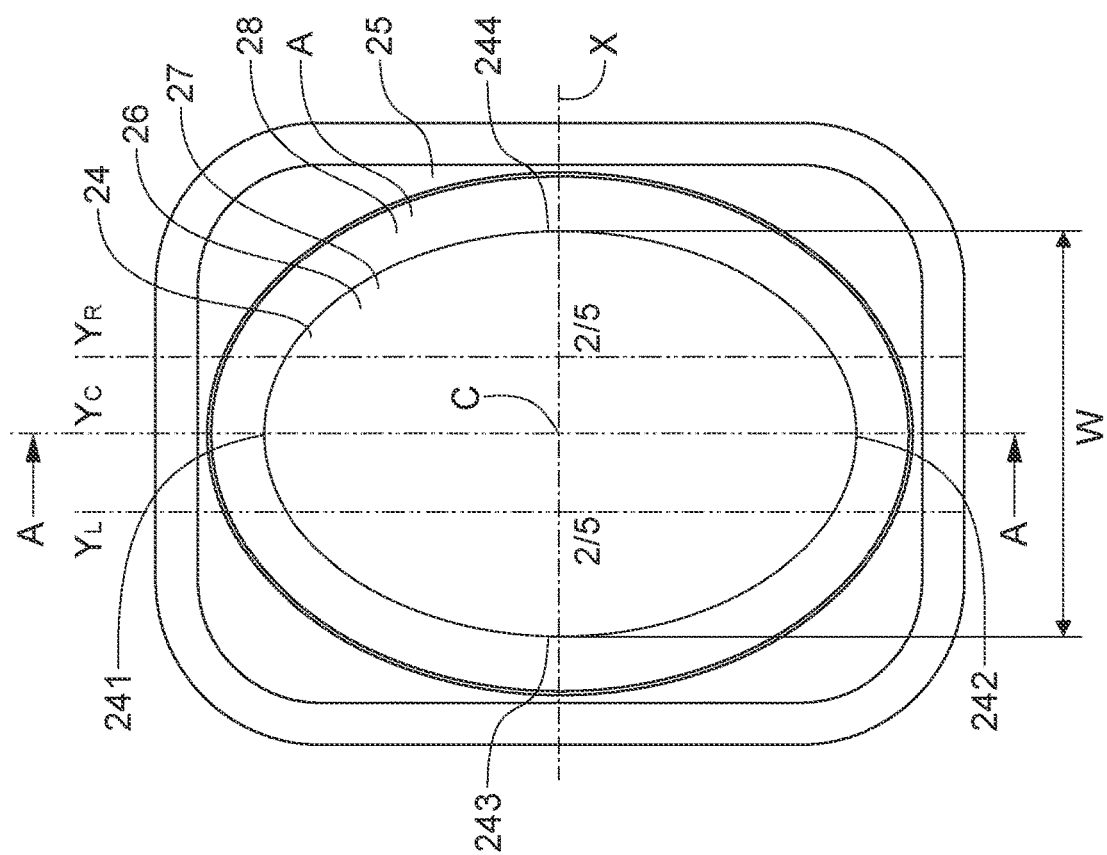
FIG. 2B is a side cross section view of the container of FIG. 2A.
Figure 2A:
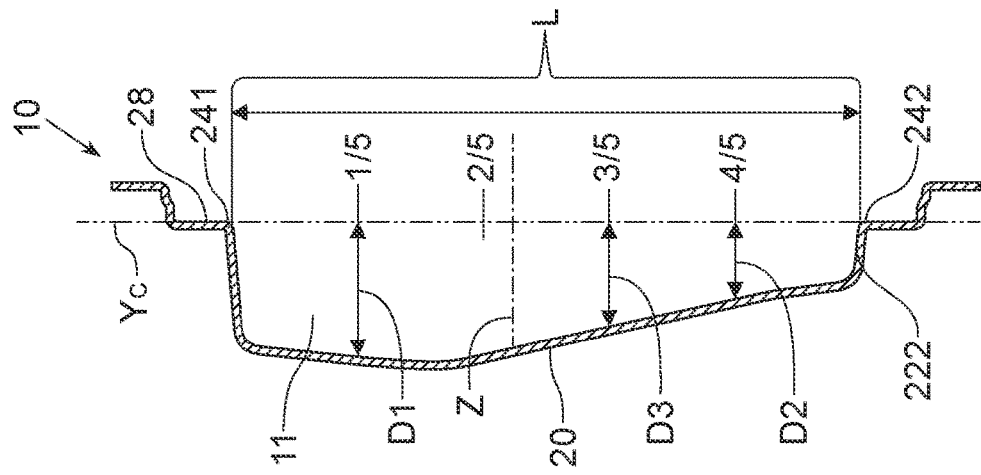
FIG. 2A is a top view of a container of the volatile composition dispenser of FIG. 1.
Figure 11:
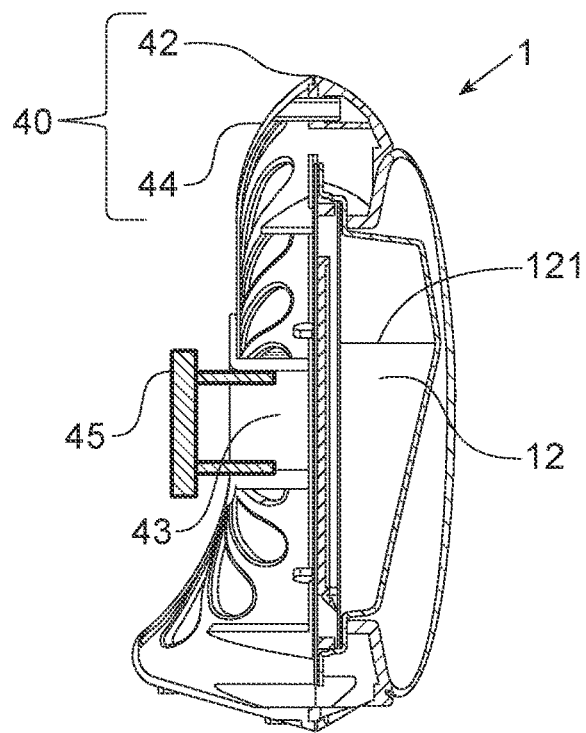
FIG. 11 is a side section view of a variation of a volatile composition dispenser according to the present invention.

FIG. 2A is a top view of a container 10 of the dispenser 1 of FIG. 1 and FIG. 2B is a side cross section view of the container 10. Referring to FIG. 2A, the side walls 22 have a circumferential inner edge 24 defining a reservoir opening 26. A planar surface 28 radially projects outward from the circumferential inner edge 24. The planar surface 28 may further comprise a circumferential outer edge 25 opposing the circumferential inner edge 24 to define a planar surface area, A therein between. The planar surface area A is configured for attaching the vapor impermeable substrate 14 in a configuration of a dispenser 1 such as shown in FIG. 11. The planar surface area A may also be configured for attaching the membrane 13 in a configuration of a dispenser such as shown in FIG. 1.

Referring to FIG. 2A, the reservoir opening 26 comprises a reservoir opening plane 27 having a center longitudinal axis $Y_C$ extending along a length, L of the reservoir opening plane 27 between opposing circumferential inner edges 24 and through a centroid, C of the reservoir opening plane 27. Referring to FIG. 1, the reservoir opening plane 27 is represented by a dotted line and a perfume surface level 16 of the perfume composition 12 in FIG. 1 is substantially horizontal. The perfume composition 12 is configured in an amount to define a head space 17 between the reservoir opening plane 27 and the perfume surface level 16 of the perfume composition 12. In FIG. 2A, the circumferential inner edges 24 may comprise a pair of opposing circumferential inner edges 241, 242, and another pair of opposing circumferential inner edges 243, 244. The circumferential inner edges 241, 242, 243, 244 are shown as a continuous circumferential edge as the reservoir opening plane 27 is shaped in a substantially elliptical shape. However, it will be appreciated that the circumferential inner edges may be easily configured to form other geometrical shapes such as a rectangular, a square, or other known shapes.

Referring to FIG. 2B, a first depth (D1) between the bottom wall 20 and the reservoir opening plane 27 is measured orthogonal to the center longitudinal axis $Y_C$ and ⅕ of the length from a first circumferential inner edge 241, and a second depth (D2) between the bottom wall 20 and the reservoir opening plane 27 is measured orthogonal to the center longitudinal axis $Y_C$ and ⅘ of the length from the first circumferential inner edge 241 such that D1 is greater than D2 to define an asymmetric profile of the bottom wall 20. A center latitudinal axis X extends along a width, W of the reservoir opening plane 27 between opposing circumferential inner edges 241, 242 and through the centroid, C forming a 90-degree angle with the center longitudinal axis. The reservoir 11 may comprise a length, L to width, W ratio from about 2:1 to about 7:1, preferably from about 3.5:1 to about 6.5:1, more preferably from about 4:1 to about 5.5:1. D1 and/or D2 may extend along the width, W of the reservoir opening plane 27 to define a flat surface across the center latitudinal axis X. Having the flat surface at the bottom wall 20 of the container 10 enables ease of making a pallet for positioning the container 10 within the pallet for transporting the container in a method of manufacturing a dispenser according to the present invention. An exemplary pallet is shown in FIGS. 4A, 4B, 4C.

Further, the side walls 22 include a first side wall 221 proximal to the first circumferential inner edge 241 and a second side wall 222 opposing the first side wall 221. The first side wall 221 is longer than the second side wall 222. As shown in FIG. 2B, the first side wall 221 is proximal to said first circumferential inner edge 241 and the second side wall 222 is proximal to a second circumferential edge 242, wherein the center longitudinal axis ($Y_C$) intersects the first circumferential inner edge 241 and the second circumferential inner edge 242. The height of the first side wall 221 is measured orthogonal to the intersection of the center longitudinal axis ($Y_C$) and the first inner circumferential edge 241 and the height of the second side wall 222 is measured orthogonal to the intersection of the center longitudinal axis ($Y_C$) and the second inner circumferential edge 242. The height of the first side wall 221 may be longer than the height of the second side wall 222, preferably the first side wall 221 is at least 10%, more preferably at least 15%, yet more preferably at least 20%, longer than the second side wall 222. However, the first side wall 221 may have the same height as the second side wall 222 such as for example, as shown in FIG. 6.

Further, as shown in FIG. 2B, the container may further comprise a third depth (D3) between the bottom wall 20 and the reservoir opening plane 27 measured orthogonal to the longitudinal axis $Y_C$ and ⅗ of the length, L from the first circumferential edge 241. D3 may be configured less than D1 and greater than D2 to define a sloped profile of at least a portion of the bottom wall 20.

A technical effect of the geometry of the container 10 is to provide a reservoir with varying depths, and preferably with side walls of different lengths for containing the perfume composition which minimizes or prevents perfume splash in a method of manufacturing a volatile composition dispenser 1.

To explain the way the container 10 works to prevent splash according to the present invention, it is helpful to understand how forces acting on the perfume composition 12 is generated during movement of the container 10 in a horizontal direction such as when the container 10 is conveyed on a conveyor belt in manufacturing. FIGS. 3A to 3C are schematic diagrams showing the container 10 comprising the perfume composition 12 after a step of dispensing the perfume composition 12 and before attaching a vapor impermeable substrate 14 to the container 10 in accordance with a method of manufacturing a volatile composition dispenser according to the present invention.

In FIGS. 3A and 3B, the container 10 is in a substantially horizontal position when placed on a support. The support may be a pallet 30 having a surface 30a, sized, spaced and positioned for transporting a container 10 during the course of manufacturing a volatile composition dispenser 1, such as shown in FIG. 4A. FIG. 3A illustrates the container 10 comprising the perfume composition 12 at rest on a conveyor belt 32 after a step of dispensing the perfume composition 12. A perfume surface level 16 of the perfume composition 12 in FIG. 3A is substantially parallel to the reservoir opening plane 27. Referring to FIG. 3A, the perfume composition 12 has a total perfume fill volume, $V_{FILL}$ configured to provide a head space 17 in the dispenser 1, wherein the head space 17 is between the perfume surface level 16 and the reservoir opening plane 27. The first side wall 221 of the container 10 faces the right side and the second side wall 222 faces the left side. Referring to FIG. 3B, when the container 10 is moved on the conveyor belt carrying the container 10, the movement of the container 10 generates an acceleration force Fx. In FIG. 3B, Fx is acting in a direction inwards into the paper. When the conveyer belt is stopped for positioning the container 10 at a next station for attaching the vapor permeable substrate 14 or the membrane 13, the perfume composition 12 in the container 10 experiences an acceleration and therefore, the perfume surface level 16 may be tilted at an angle, θ with respect to the reservoir opening plane 27 due to the horizontal acceleration force Fx in the perfume composition 12. Specifically, the perfume surface level 16 drops relative to the reservoir opening plane 27 at the first side wall 221 of the container 10 and rises relative to the reservoir opening plane 27 at the second side wall 222 of the container 10.

Without wishing to be bound by theory, a technical effect of having D1 longer than D2 enables a head space 17 sufficient for minimizing splash when the container containing the perfume composition is moved after filling and stopped at the next station for subsequent process steps in a method of manufacturing a volatile composition dispenser according to the present invention.

FIGS. 4A, 4B and 4C are schematic diagrams showing steps of a method of manufacturing a volatile composition dispenser 1 according to the present invention. The dispenser 1 described with respect to FIGS. 4A, 4B and 4C have substantially the same components as the dispenser 1 of FIG. 9. However, it will be clear from the following description that the method can be easily modified for manufacturing the dispenser 1 of FIG. 1. FIG. 4A illustrates a first step 4A of the method in which the container 10 is positioned on a pallet 30 such that the bottom wall 20 is adjacent to the pallet 30 and the reservoir opening plane 27 faces upward away from the pallet 30 and perfume composition 12 is dispensed into the container 10 through a nozzle 31 in fluid communication with a tank 33 containing perfume composition 12.

The perfume composition 12 may be dispensed up to a level to define a head space 17 between the perfume surface level 16 and the reservoir opening plane 27. A total perfume fill volume, $V_{FILL}$ of the perfume composition 12 may be 75%, preferably 70%, more preferably 65%, yet more preferably 60% of a total internal reservoir volume, $V_r$ of the reservoir 11. The total internal reservoir volume, $V_r$ is defined as $$V_r = \text{Surface Area (S.A.) of the reservoir opening plane} \times \text{Average Depth (Avg. D.) of the reservoir.}$$

The head space 17 comprises a headspace volume of at least 25%, preferably at least 30%, more preferably at least 35%, even more preferably at least 40% of the total internal reservoir volume, $V_r$. An advantage of having the minimum headspace volume in the above described percentages is that it enables the conveyor belt to be operated at a maximum line speed to increase production output of the dispensers' and minimizing perfume splash. The surface area (S.A.) of the reservoir opening plane 27 depends on a geometry or shape of the reservoir opening plane 27. For example, referring to FIG. 2A, the reservoir opening plane 27 has an elliptical shape and the surface area of the reservoir opening plane 27 will be calculated accordingly based on known mathematical formulae. The perfume composition 12 may be configured in an amount from about 2 ml to 50 ml, preferably 4 ml to 30 ml, more preferably 6 ml to 20 ml, even more preferably 6.5 ml to 8 ml. Optionally outflow from the nozzle 31 may be directed in closer proximity to D1 compared to D2 to minimize splash during filling.

FIG. 4B illustrates a second step 4B of the method in which the container 10 containing the perfume composition 12 is transported to a station for attaching a vapor impermeable substrate 14 to the planar surface 28 of the container 10. As described in the above with respect to FIGS. 3A, 3B and 3C, perfume splashing is minimized between steps 4A and 4B thereby enabling an optimal perfume fill volume and prevent perfume splash on the planar surface 28 of the container 10 for attaching the vapor impermeable substrate 14, as well as preventing splash on an outer periphery 15 of the container 10.

FIG. 4C illustrates a third step 4C in which the membrane 13 is attached to the container such that the vapor impermeable substrate 14 is between the reservoir opening plane 27 and the membrane 13. The method may include an optional step of placing a rupture mechanism 50 as described with respect to FIG. 9 prior to step 4C, such that the rupture mechanism 50 is disposed between the membrane 13 and the vapor impermeable substrate 14.

The conveyor belt 32 may be operated at a line speed of greater than or equal to 14 cycles per minute, preferably 14 to 20 cycles per minute, more preferably 16 to 20 cycles per minute, yet more preferably 18 to 20 cycles per minute. An effect of operating the conveyor belt at a line speed of 20 cycles per minute is that it enables an increased production output relative to a lower line speed which will require addition of new lines to achieve the same increased production out, thereby enabling a savings in capital investments.

Figure 5A:
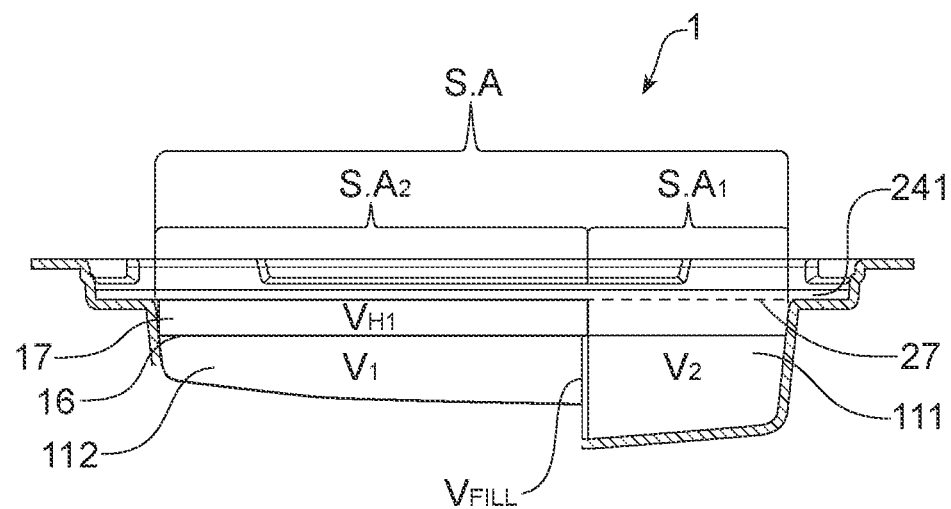
FIG. 5A is a side section view of an assembled volatile composition dispenser according to the present invention in a horizontal orientation when the dispenser is placed on a support.

FIG. 5A is a side section view of an assembled dispenser 1 according to the present invention in a horizontal orientation when the dispenser 1 is placed on a support and FIG.

5B is a side section view of the dispenser 1 in a vertical orientation when the dispenser 1 is placed on a support.

Referring to FIG. 5A, the surface area (S.A.) of the reservoir opening plane 27 comprises a first surface area, $SA_1$ and a second surface area, $SA_2$, wherein $SA_1$ is based on ⅕ of the length from the first circumferential inner edge 241 to define a reservoir deep region 111 and $SA_2$ is based on ⅘ of the length from the first circumferential inner edge 241 to define a reservoir shallow region 112 relative to the reservoir deep region 111, wherein $SA_1 < SA_2$. Further, the head space 17 has a total head space volume, $V_H$, between the perfume surface level 16 and the reservoir opening plane 27. There is a first perfume volume $V_1$ in the reservoir shallow region 112 and $SA_2$ of the reservoir opening plane 27. There is a second perfume fill volume $V_2$ in the reservoir deep region 111, wherein total perfume fill volume, $V_{FILL} = V_1 + V_2$, assuming no loss of perfume composition due to splash.

Further, the head space volume comprises a first head space volume, $V_{H1}$, wherein $V_{H1}$ is defined as $V_{H1}$=Total internal reservoir volume $V_r$–Volume of the perfume composition in the reservoir shallow region;

wherein $V_{H1}$ is less than or equal to a Volume of the perfume composition $V_2$ in the deep reservoir region;

wherein the total perfume fill volume, $V_{FILL}$ is defined as total perfume fill volume=Volume of the perfume composition in the reservoir shallow region+Volume of the perfume composition in the reservoir shallow region.

Preferably, $V_{H1}$ is at least 1 ml, more preferably $V_{H1}$ is from 1 ml to 3 ml.

Figure 5B:
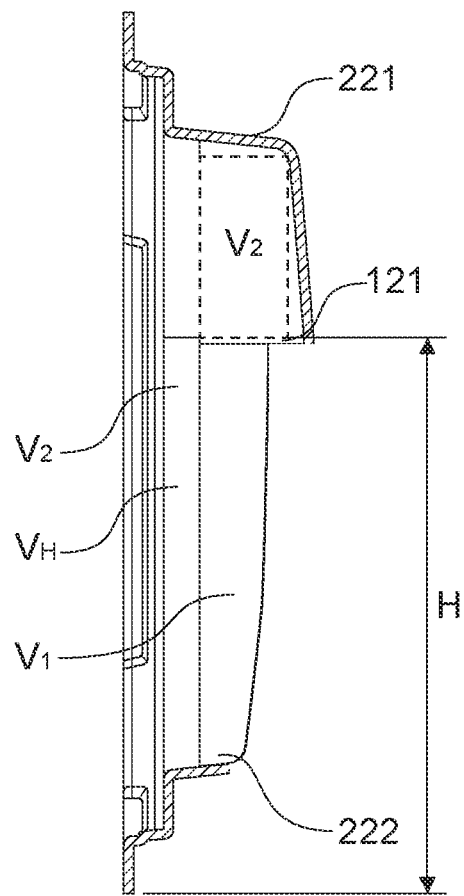
FIG. 5B is a partial perspective view of the volatile composition dispenser in a vertical orientation when the dispenser is placed on a support.

Specifically, referring to FIG. 5B, the dispenser 1 is positioned in a vertical orientation such that the reservoir shallow region 112 is adjacent to the support supporting the dispenser 1 and the reservoir deep region 111 is above the reservoir shallow region 112. In this vertical orientation, the second perfume fill volume $V_2$ moves into the head space volume $V_H$ to set a vertical level 121 of the perfume composition 12 in the dispenser 1. For example, if $V_{FILL}$=6.5 ml, $V_2$ may be configured to be less than or equal to $V_H$, such as for example, $V_H$ may be 2.75 ml, $V_2$ and $V_1$ may be configured to be 2.75 ml and 3.75 ml respectively so that when the dispenser 1 is placed in a vertical orientation, $V_2$ flows into the head space volume $V_H$ to define a vertical perfume height, H between the vertical level 121 and a base of the dispenser 1. The vertical perfume height, H functions as a visual indicator demonstrating a product content and as the H reduces upon use of the dispenser 1 demonstrating start to the end of life of the dispenser 1. Further, at least 20%, preferably 30%, more preferably 50% of a surface area of the bottom wall 12 comprising the reservoir deep region 111 is at least partially transparent, preferably transparent.

FIG. 6 is a side section view of a variation of a container 10 of a volatile composition dispenser 1 according to the present invention in a horizontal orientation when placed on a support. Specifically, the container 10 may comprise a third depth (D3) between the bottom wall 20 and the reservoir opening plane 27 measured orthogonal to the longitudinal axis $Y_C$ and ⅗ of the length from the first circumferential edge 241 such that D3 is greater than D2, preferably D3 is equal to D1 to define a trapezoidal profile of the bottom wall 20.

FIG. 7A is a perspective view of a variation of a container 10 of a volatile composition dispenser 1 according to the present invention in a vertical orientation when placed on a support and FIG. 7B is a side section view of the container 10 of FIG. 7A. The container 10 of FIG. 7A has substantially the same features as the container of FIG. 2A and differs in the following additional components. Specifically, the container 10 may comprise a left longitudinal axis, $Y_L$ parallel to the center longitudinal axis $Y_C$ between opposing circumferential inner edges. As shown in FIG. 2A, a center latitudinal axis X extending along a width of the reservoir opening plane 27 between opposing circumferential inner edges 241, 242 and through the centroid, C forming a 90-degree angle with the center longitudinal axis ($Y_C$). A left longitudinal axis ($Y_L$) parallel to the center longitudinal axis ($Y_C$) between opposing circumferential inner edges 243, 244, wherein the left longitudinal axis ($Y_L$) is located ⅖ of the width of the center latitudinal axis X from a third circumferential inner edge 243. Referring to FIG. 7B, a fourth depth (D4) between the bottom wall (20) and the reservoir opening plane (27) is measured orthogonal to the left longitudinal axis ($Y_L$) and ⅕ of the length of the left longitudinal axis ($Y_L$) from the first circumferential inner edge (241), and a fifth depth (D5) between the bottom wall (20) and the reservoir opening plane (27) is measured orthogonal to the left longitudinal axis ($Y_L$) and ⅘ of the length of the left longitudinal axis ($Y_L$) from the first circumferential inner edge (241), wherein D4 is longer than D5.

Figure 8A:
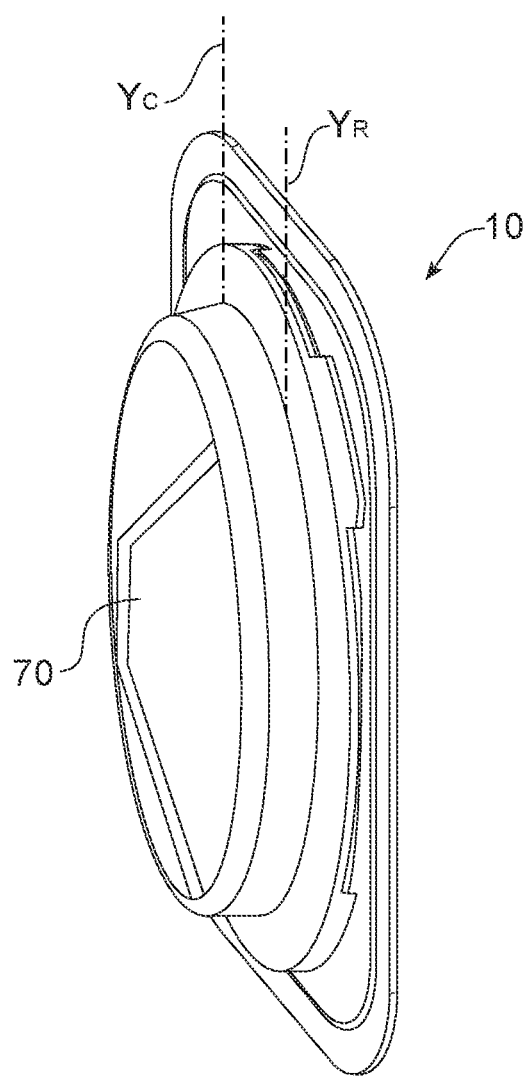
FIG. 8A is a perspective view of a variation of a container of a volatile composition dispenser according to the present invention.
Figure 8B:
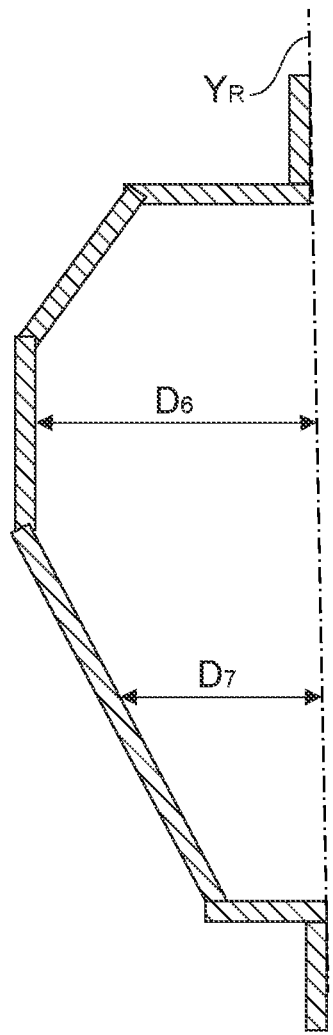
FIG. 8B is a side cross section of the container of FIG. 8A.

FIG. 8A is a perspective view of a variation of a container 10 of a volatile composition dispenser according to the present invention in a vertical orientation when placed on a support and FIG. 8B is a side section view of the container 10 of FIG. 8A. The container 10 of FIG. 8A has substantially the same features as the container of FIG. 7A and differs in the following additional components. Referring to FIG. 2A, the container 10 may also comprise a right longitudinal axis $Y_R$ parallel to the center longitudinal axis ($Y_C$) between opposing circumferential inner edges 243, 244, wherein the right longitudinal axis ($Y_R$) is located ⅖ of the width from a fourth inner circumferential edge 244. Referring to FIG. 8B, a sixth depth D6 is between the bottom wall 20 and the reservoir opening plane 27. D6 is measured orthogonal to the right longitudinal axis ($Y_R$) and ⅕ of the length of the right longitudinal axis ($Y_R$) from the first circumferential inner edge 241, and a seventh depth D7 between the bottom wall 20 and the reservoir opening plane 27 is measured orthogonal to the right longitudinal axis ($Y_R$) and ⅘ of the length of the right longitudinal axis ($Y_R$) from the first circumferential inner edge 241, wherein D6 is longer than D7. Although FIGS. 7A, 7B, 8A, 8B show configurations of a container having a protuberance 70 extending from the outer surface of the bottom wall 20, it will be appreciated that the container can be molded in a way such that the protuberance may extend in an inward direction within the reservoir 11 to achieve similar technical effect of preventing splash as described hereinbefore.

The dispenser 1 of the present invention can be configured for use in a variety of applications to deliver a perfume composition 12 to the atmosphere as long as the perfume composition 12 can vaporize from the membrane 13 into the air.

Accordingly, the specific physical properties of the membrane 13 may be chosen based on the specific desired use of the dispenser 1, designed to be activated by peeling off the vapor impermeable substrate 14 or by rupturing the vapor impermeable substrate 14. Membranes and vapor impermeable substrates designed to be releasably attached are known and will not be further described. Examples of suitable physical parameters of the membrane 13 and the vapor impermeable substrate 14 suitable for a dispenser 1 designed to be activated by rupturing the vapor impermeable substrate 14 will be described hereinafter in the description.

The membrane 13 may be a microporous membrane and comprise an average pore size of about 0.01 to about 1 microns, about 0.01 to about 0.06 microns, from about 0.01 to about 0.05 microns, about 0.01 to about 0.04 microns, about 0.01 to about 0.03 microns, about 0.02 to about 0.04 microns, or about 0.02 microns. Further, the membrane 12 may be filled with any suitable filler and plasticizer known in the art. Fillers may include finely divided silica, clays, zeolites, carbonates, charcoals, and mixtures thereof. An example of a filled membrane is an ultra-high molecular weight polyethylene (UHMWPE) membrane filled with silica, such as those described in U.S. Pat. No. 7,498,369. Although any suitable fill material and weight percentage may be used, typical fill percentages for silica, may be between about 50% to about 80%, about 60% to about 80%, about 70% to about 80%, or about 70% to about 75% of the total weight of the membrane. Examples of suitable membrane thicknesses include, but are not limited to between about 0.01 mm to about 1 mm, between about 0.1 mm to 0.4 mm, about 0.15 mm to about 0.35 mm, or about 0.25 mm. Still further, an evaporative surface area of the membrane 12 may be about 2 $cm^2$ to about 100 $cm^2$, about 2 $cm^2$ to about 25 $cm^2$, about 10 $cm^2$ to about 50 $cm^2$, about 10 $cm^2$ to about 45 $cm^2$, about 10 $cm^2$ to about 35 $cm^2$, about 15 $cm^2$ to about 40 $cm^2$, about 15 $cm^2$ to about 35 $cm^2$, about 20 $cm^2$ to about 35 $cm^2$, about 30 $cm^2$ to about 35 $cm^2$, about 35 $cm^2$.

The vapor impermeable substrate 14 may be made of any material that can be ruptured with a pre-determined applied force, with or without the presence of an element, such as rupture element, to aid in such rupture. The planar surface may further comprise a circumferential outer edge opposing said circumferential inner edge, to define a planar surface area therein between, wherein the planar surface area is configured for attaching the vapor impermeable substrate.

In embodiments where the vapor impermeable substrate 14 is intended to contain the volatile composition when the dispenser 1 is not in use, the vapor impermeable substrate 14 may be made from any suitable barrier material that reduces or prevents evaporation of the perfume composition 12. Such materials may be impermeable to vapors and liquids. Suitable barrier materials for the vapor impermeable substrate 14 include, but are not limited to coated or uncoated films, such as polymeric films, webs, foils, and composite materials such as foil/polymeric film laminates. An example of a foil that may be used as a barrier material is a micron aluminum foil including a nitrocellulose protective lacquer, a polyurethane primer, and a 15 g/m2 polyethylene coating (Lidfoil 118-0092), available from Alcan Packaging. Suitable polymeric films include, but are not limited to, polyethylene terephtalate (PET) films, acrylonitrile copolymer barrier films such as, for example, those sold under the tradename Barex® by INOES, ethylene vinyl alcohol films, and combinations thereof. It is also contemplated that coated barrier films may be utilized as the vapor impermeable substrate 14. Such coated barrier films include, but are not limited to, metallized PET, metalized polypropylene, silica or alumina coated film.

Figure 9:
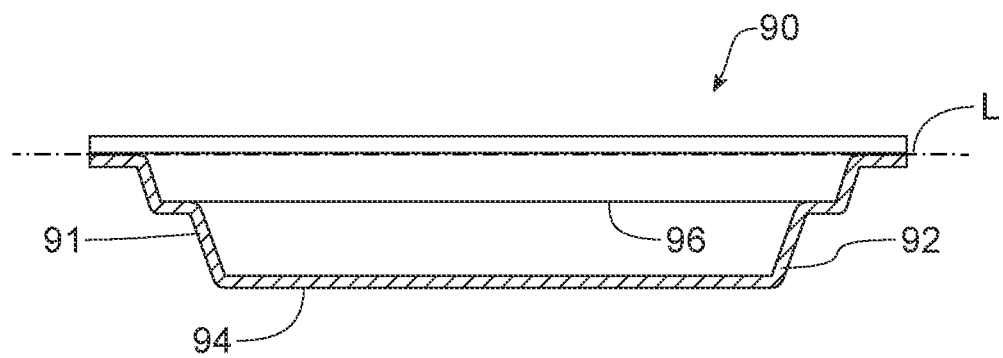
FIG. 9 is a side cross section of a conventional dispenser.

FIG. 10 is a side section view of components in a variation of a dispenser 1 according to the present invention without the perfume composition. The dispenser 1 of FIG. 9 comprise substantially the same features as the dispenser 1 of FIG. 1 with additional components described as follows. Referring to FIG. 9, the dispenser 1 comprises a rupture mechanism 50 disposed between the membrane 13 and the vapor impermeable substrate 14, wherein the rupture mechanism 50 has one or more rupture elements 52 for rupturing the vapor impermeable substrate 14.

FIG. 11 is a side section view of a variation of a dispenser 1 according to the present invention. The dispenser 1 of FIG. 10 comprise substantially the same features as the dispenser 1 of FIG. 9 with additional components described as follows. Referring to FIG. 10, the dispenser 1 may further comprise a housing 40 having a front cover 42 and a rear frame 44, the front cover 42 and the rear frame 44 defining an interior space. The rear frame 44 is provided with a frame opening 43 (hereinafter "opening") located substantially in the centre of the rear frame 44. An actuator 45 movable relative to the housing 40 is provided for activating the dispenser 1. The actuator 45 may be, for example, a push button 45 (hereinafter "button") disposed within the opening 43 and is movable with respect to the rear frame 44 for enabling a user to activate the dispenser 1. The container 10 containing the perfume composition 12 is located within the housing 40. The front cover 42 comprises a window configured for displaying the perfume composition 12 in the container 10 such that the vertical level of the perfume composition 12 is visible to the consumers. The dispenser 1 may further comprise a front plate 46 releasably attached to the front cover 42, wherein the front plate 46 may include decorative motifs for providing an aesthetic effect to the dispenser 1. The front plate 46 may be partially transparent to enable viewing of the vertical level of the perfume composition 12

Perfume Composition

The dispenser 1 of the present invention may comprise an air freshening composition, wherein the air freshening composition comprise up to 100%, about 4% to about 100%, about 15% to about 100%, about 65% to 86%, of the perfume composition 12 by weight of the air freshening composition.

The perfume composition 12 may comprise a viscosity of from about 1.0 cP to less than about 25 cP, preferably about 1.0 cP to less than about 20 cP, at 25 degrees Celsius.

The perfume composition 12 may comprise a mixture of carbonyl containing compounds. The mixture of carbonyl containing compounds may be present in an amount of from about equal to or greater than 0.01% to about less than or equal to 100%, in an amount from about 0.01% to 50%, from about 1% to 40%, from about 4% to 25%, from about less than or equal to 5% to equal to or less than 25% by weight of the perfume composition. An effect of having less than 25% by weight of the carbonyl containing compounds is to enable formulation space for adding optional ingredients described hereinafter such as perfume raw materials to provide a hedonic experience.

The vapor pressure of the volatile carbonyl containing compounds may be greater than or equal to 0.025 torr, about 0.025 torr to about 30 torr, measured at 25 degrees Celsius. The vapor pressure of individual volatile carbonyl containing compounds can be calculated using the Advanced Chemistry Development Labs ("ACD") (Toronto, Canada) VP computational model, version 14.02 providing vapor pressure (VP) values at 25 degrees Celsius expressed in unit of torr. The volatile carbonyl containing compound may be selected from the group consisting of: volatile aldehydes, ketones and mixtures thereof. Exemplary volatile aldehydes and ketones are listed in the following description and are named according to the method of naming organic chemical compounds as recommended by the International Union of Pure and Applied Chemistry (IUPAC).

The carbonyl containing compound may comprise volatile aldehydes. Aldehydes that are partially volatile may be considered a volatile aldehyde as used herein. Exemplary volatile aldehydes which may be used include, but are not limited to, aldehydes as shown in Table 1 below. The carbonyl containing compound may also comprise ketones. Exemplary ketones which may be used in the volatile material include, but are not limited to ketones shown in Table 2 below.

TABLE 1

| CAS | IUPAC Name | Vapor Pressure (torr) @ 25 degrees Celsius |
|---|---|---|
| 04-55-2 | (E)-3-phenylprop-2-enal | 0.080 |
| 100-52-7 | Benzaldehyde | 0.13 |
| 122-03-2 | 4-propan-2-ylbenzaldehyde | 0.031 |
| 123-11-5 | 4-methoxybenzaldehyde | 0.021 |
| 557-48-2 | (2E,6Z)-nona-2,6-dienal | 0.18 |
| 6728-26-3 | (E)-hex-2-enal | 10.66 |
| 5392-40-5 | (2E)-3,7-dimethylocta-2,6-dienal | 0.13 |
| 2363-89-5 | (E)-oct-2-enal | 0.99 |
| 21662-13-5 | (2E,6Z)-dodeca-2,6-dienal | 0.004 |
| 2463-53-8 | non-2-enal | 0.21 |
| 1335-66-6 | 2,4,6-trimethylcyclohex-3-ene-1-carbaldehyde; 3,5,6-trimethylcyclohex-3-ene-1-carbaldehyde | 2.64 |

TABLE 1-continued

| CAS | IUPAC Name | Vapor Pressure (torr) @ 25 degrees Celsius |
|---|---|---|
| 33885-52-8 | 3-(6,6-dimethyl-4-bicyclo[3.1.1]hept-3-enyl)-2,2-dimethylpropanal | 0.028 |
| 124-19-6 | Nonanal | 0.37 |
| 65405-70-1 | (E)-dec-4-enal | 0.35 |
| 106-72-9 | 2,6-dimethylhept-5-enal | 0.48 |
| 2277-19-2 | (Z)-non-6-enal | 0.22 |
| 3613-30-7 | 7-methoxy-3,7-dimethyloctanal | 0.040 |
| 6784-13-0 | 3-(4-methylcyclohex-3-en-1-yl)butanal | 0.11 |
| 106-23-0 | 3,7-dimethyloct-6-enal | 0.14 |
| 19009-56-4 | 2-methyldecanal | 0.053 |
| 68039-49-6 | 2,4-dimethylcyclohex-3-ene-1-carbaldehyde | 0.73 |
| 112-45-8 | undec-10-enal | 0.019 |
| 71077-31-1 | 4,8-dimethyldeca-4,9-dienal | 0.019 |
| 124-13-0 | Octanal | 1.14 |
| 112-44-7 | Undecanal | 0.037 |
| 112-31-2 | Decanal | 0.12 |
| 143-14-6 | undec-9-enal | 0.011 |
| 62439-41-2 | 6-methoxy-2,6-dimethylheptanal | 0.130 |
| 33885-51-7 | 3-(6,6-dimethyl-4-bicyclo[3.1.1]hept-3-enyl)propanal | 0.039 |

TABLE 2

| CAS | IUPAC Name | Vapor Pressure (VP), torr @ 25° C. |
|---|---|---|
| 1125-21-9 | 2,6,6-trimethylcyclohex-2-ene-1,4-dione | 0.158 |
| 10373-78-1 | 4,7,7-trimethylbicyclo[2.2.1]heptane-2,3-dione | 0.0817 |
| 1193-79-9 | 1-(5-methylfuran-2-yl)ethanone | 0.301 |
| 765-70-8 | 3-methylcyclopentane-1,2-dione | 0.978 |
| 98-86-2 | 1-phenylethanone | 0.299 |
| 600-14-6 | pentane-2,3-dione | 26.416 |
| 4077-47-8 | 4-methoxy-2,5-dimethylfuran-3-one | 0.103 |
| 3658-77-3 | 4-hydroxy-2,5-dimethylfuran-3-one | 0.032 |
| 1196-01-6 | (1S,5S)-2,6,6-trimethylbicyclo[3.1.1]hept-2-en-4-one | 0.0773 |
| 18309-32-5 | (1R,5R)-2,6,6-trimethylbicyclo[3.1.1]hept-2-en-4-one | 0.0773 |
| 78-59-1 | 3,5,5-trimethylcyclohex-2-en-1-one | 0.15 |
| 2758-18-1 | 3-methylcyclopent-2-en-1-one | 2.741 |
| 2244-16-8 | (5S)-2-methyl-5-prop-1-en-2-ylcyclohex-2-en-1-one | 0.0656 |
| 6485-40-1 | (5R)-2-methyl-5-prop-1-en-2-ylcyclohex-2-en-1-one | 0.0656 |
| 141-79-7 | 4-methylpent-3-en-2-one | 8.757 |
| 99-49-0 | 2-methyl-5-prop-1-en-2-ylcyclohex-2-en-1-one | 0.0656 |
| 1072-83-9 | 1-(1H-pyrrol-2-yl)ethanone | 0.11 |
| 89-82-7 | (5R)-5-methyl-2-propan-2-ylidenecyclohexan-1-one | 0.0934 |
| 2550-26-7 | 4-phenylbutan-2-one | 0.0557 |
| 2308-18-1 | 3-methylbutyl 3-oxobutanoate | 0.167 |
| 513-86-0 | 3-hydroxybutan-2-one | 1.92 |
| 81786-73-4 | (Z)-3,4,5,6,6-pentamethylhept-3-en-2-one | 0.0275 |
| 4906-24-5 | 3-oxobutan-2-yl acetate | 2.069 |
| 105-45-3 | methyl 3-oxobutanoate | 1.543 |
| 141-97-9 | ethyl 3-oxobutanoate | 0.89 |
| 5524-05-0 | (2R,5R)-2-methyl-5-prop-1-en-2-ylcyclohexan-1-one | 0.107 |
| 7764-50-3 | 2-methyl-5-prop-1-en-2-ylcyclohexan-1-one | 0.107 |
| 5948-04-9 | (2S,5S)-2-methyl-5-prop-1-en-2-ylcyclohexan-1-one | 0.107 |
| 55739-89-4 | 2-ethyl-4,4-dimethylcyclohexan-1-one | 0.25 |
| 25304-14-7 | 1-(3,3-dimethylcyclohexyl)ethanone | 0.287 |
| 36977-92-1 | (2S,5S)-5-methyl-2-propan-2-ylcyclohexan-1-one | 0.256 |
| 89-80-5 | (2S,5R)-5-methyl-2-propan-2-ylcyclohexan-1-one | 0.256 |
| 65443-14-3 | 2,2,5-trimethyl-5-pentylcyclopentan-1-one | 0.0261 |
| 873-94-9 | 3,3,5-trimethylcyclohexan-1-one | 0.582 |
| 4884-24-6 | 2-cyclopentylcyclopentan-1-one | 0.0588 |
| 546-80-5 | (1S,4R,5R)-4-methyl-1-propan-2-ylbicyclo[3.1.0]hexan-3-one | 0.323 |
| 16587-71-6 | 4-(2-methylbutan-2-yl)cyclohexan-1-one | 0.0649 |
| 76-22-2 | 4,7,7-trimethylbicyclo[2.2.1]heptan-3-one | 0.225 |
| 110-93-0 | 6-methylhept-5-en-2-one | 1.277 |
| 111-13-7 | octan-2-one | 1.725 |
| 7787-20-4 | (1S,4R)-2,2,4-trimethylbicyclo[2.2.1]heptan-3-one | 0.463 |
| 110-43-0 | heptan-2-one | 4.732 |
| 1195-79-5 | 2,2,4-trimethylbicyclo[2.2.1]heptan-3-one | 0.463 |

TABLE 2-continued

| CAS | IUPAC Name | Vapor Pressure (VP), torr @ 25° C. |
|---|---|---|
| 541-85-5 | 5-methylheptan-3-one | 2.444 |
| 106-68-3 | octan-3-one | 1.504 |

Table 3 shows a mixture of volatile aldehydes suitable for use in the dispenser 1 of the present invention, the mixture is referred to herein as Accord A.

TABLE 3

Accord A

| CAS No. | Material Name | Weight % by weight of the Volatile Material | VP (torr) @ 25° C. |
|---|---|---|---|
| 6728-26-3 | (E)-hex-2-enal | 1 to 4 | 10.66 |
| 1335-66-6 | 2,4,6-trimethylcyclohex-3-ene-1-carbaldehyde; 3,5,6-trimethylcyclohex-3-ene-1-carbaldehyde | 4 to 8 | 2.64 |
| 124-13-0 | octanal | 7 to 12 | 1.14 |
| 68039-49-6 | 2,4-dimethylcyclohex-3-ene-1-carbaldehyde | 10 to 20 | 0.73 |
| 106-72-9 | 2,6-dimethylhept-5-enal | 10 to 20 | 0.48 |
| 2277-19-2 | (Z)-non-6-enal | 0.1 to 0.3 | 0.22 |
| 557-48-2 | (2E,6Z)-nona-2,6-dienal | 0.3 to 1.0 | 0.18 |
| 100-52-7 | benzaldehyde | 8 to 13 | 0.13 |
| 5392-40-5 | (2E)-3,7-dimethylocta-2,6-dienal | 7 to 12 | 0.13 |
| 112-31-2 | decanal | 10 to 20 | 0.12 |
| 30772-79-3 | 4,7-Methanoindan-1-carboxaldehyde | 10 to 20 | 0.05 |
| | Total by weight of the Volatile Material | 100% | |

Table 4 shows a further mixture of volatile aldehydes suitable for use in the dispenser of the present invention, the mixture is referred to herein as Accord B.

TABLE 4

Accord B

| CAS | Material Name | Wt % by weight of the Volatile Material | VP (torr) @ 25° C. |
|---|---|---|---|
| 6728-26-3 | (E)-hex-2-enal | 0.5 to 2.0 | 10.66 |
| 124-13-0 | octanal | 3 to 10 | 1.14 |
| 110-41-8 | 2-methylundecanal | 1 to 5 | 0.015 |
| 100-52-7 | benzaldehyde | 10 to 20 | 0.13 |
| 106-72-9 | 2,6-dimethylhept-5-enal | 3 to 8 | 0.48 |
| 68039-49-6 | 2,4-dimethylcyclohex-3-ene-1-carbaldehyde | 9 to 15 | 0.73 |
| 124-19-6 | nonanal | 1 to 3 | 0.37 |
| 1335-66-6 | 2,5,6-trimethylcyclohex-3-ene-1-carbaldehyde | 5 to 10 | 2.64 |
| 557-48-2 | (2E,6Z)-nona-2,6-dienal | 0.2 to 1.2 | 0.182 |
| 112-31-2 | decanal | 7 to 15 | 0.12 |
| 5392-40-5 | (E)-3,7-dimethylocta-2,6-dienal | 10 to 20 | 0.13 |
| 112-45-8 | undec-10-enal | 1 to 5 | 0.019 |
| 112-54-9 | dodecanal | 1 to 6 | 0.007 |
| 123-11-5 | 4-methoxybenzaldehyde | 10 to 20 | 0.021 |
| | Total by weight of the Volatile Material | 100% | |

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

EXAMPLES

Test equipment/materials and test dispenser samples are first described under Materials, then the Test Method is provided, and lastly results are discussed. Data is provided demonstrating the dispensers of the present invention having improved splash control and achieves a desired vertical fill height. Equipment and materials used in the Test Method described hereinafter are listed in Table 5 below. The perfume compositions provided in the inventive and comparative samples are prepared using conventional methods. FIG. 9 shows a configuration of a conventional dispenser 90 used as a comparative sample in the test. As shown in FIG. 9, the conventional dispenser 90 differ from the dispenser 1 of FIG. 5A in that the conventional dispenser 90 has a container 92 having side walls 91 of uniform height and an uniform depth (D) between a bottom wall 94 and a reservoir opening plane 96 of the container 92, wherein a height of the side walls 91 and D is measured orthogonal to a longitudinal axis (L) of the container 92.

Materials

TABLE 5

Equipment/Materials

| Equipment/Materials | Technical Specifications |
|---|---|
| Conveyor Belt | Monolab Main Automatic Machine<br>Manufacturer: Monolab<br>Model: MB961XL<br>Serial Number: B2.09.009 |
| Perfume Filling Station | Technical Specifications are not disclosed by the manufacturer. Filling station comprising a nozzle in fluid communication with a tank containing a perfume composition |
| Perfume Composition for Perfume Filing Station | Perfume composition having a viscosity of from 1.0 cp to less than 25 cp at 25 degrees Celsius. |
| Comparative Sample #1 | Conventional Dispenser with configuration based on FIG. 9 with perfume composition having a viscosity of from 1.0 cp to less than 25 cp at 25 degrees Celsius. |
| Comparative Sample #2 | Conventional Dispenser with configuration based on FIG. 9 with perfume composition having a viscosity of from 1.0 cp to less than 25 cp at 25 degrees Celsius. |
| Inventive Sample #3 | Inventive Dispenser with configuration based on FIG. 5A with perfume composition having a viscosity of from 1.0 cp to less than 25 cp at 25 degrees Celsius. |

Test Method

Perfume Fill Performance Test Method

This test method is to determine a maximum line speed for containers containing perfume composition and having different head space volumes or head space gap between the perfume surface level and the reservoir opening plane. The test method is performed under the following test conditions: at an average temperature of 20° C. to 25° C. The steps for performing the test are illustrated in FIGS. 4A to 4C and include:

1) positioning a container on a pallet;
2) moving the pallet comprising the container on a conveyor belt to a filling station comprising a nozzle in fluid communication with a tank containing a perfume composition;
3) attaching a vapor impermeable substrate to the container comprising the dispensed perfume composition; and
4) attaching a membrane to form a dispenser.

Example

Comparative Samples #1, #2 and Inventive Sample #3 of Table 5 are evaluated according to the Perfume Fill Performance Test Method described hereinbefore under Test Method.

Table 6 shows a correlation between the head space 17 in the dispenser 1 and a maximum line speed without perfume splash (cycles/minute) to achieve a desired vertical level in the perfume composition 12.

TABLE 6

| Example | Total internal reservoir volume of the reservoir, $V_r$ | Total Perfume Fill Volume (ml) | Total Perfume Fill Volume as a % of a total internal reservoir volume of the reservoir, $V_r$ | Total Head Space Volume | Maximum line speed (cycles/minute) with no splash detected | Vertical Visual Height (Perfume Fill Level in a Vertical Orientation of the Dispenser |
|---|---|---|---|---|---|---|
| Comparative Sample #1 | 10.5 ml | 6.5 ml | 60% | 4 ml | 20 | 39.7 mm |
| Comparative Sample #2 | 10.5 ml | 7.2 ml | 70% | 3.3 ml | 17 | ≥42.4 mm |
| Inventive Sample #3 | 10.5 ml | 6.5 ml | 60% | 4 ml | 20 | ≥42.4 mm |

As shown in Table 6, the results of Inventive Sample #3 demonstrate that having a configuration of the container 10 in the Inventive Sample #3 and enables an optimum total head space volume of 4 ml to prevent splash and achieves a vertical visual height of greater than or equal to 42.4 mm when Inventive Sample #3 is placed in a vertical orientation. Further, the production of Inventive Sample #3 is achieved at a maximum speed of 20 cycles/minute to optimize production output. The results of Comparative Sample #1 show a lower vertical visual height of 39.7 mm compared to Inventive Sample #3 even with the same perfume fill volume of 6.5 ml and the same head space volume of 4 ml. On the other hand, the results of Comparative Sample #2 show the same vertical visual height of 42.4 mm, but the line speed is reduced to 17 cycles per minute in order to prevent splash.

The overall results show that having a container 10 of the present invention having a first depth (D1) and a second depth (D2) between the bottom wall 20 and the reservoir opening plane 27 wherein D1 is longer than D2 helps prevent perfume splash and achieves a desired vertical visual height requirement than a configuration without D1 and D2, despite maintaining all other conditions such as demonstrated in Comparative Sample #1. Therefore, a container having D1 and D2 as described hereinbefore may be used to prevent the effect of splash in manufacturing while achieving high production output of dispensers which meet the visual vertical height requirements.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a volatile composition dispenser, the process comprising the steps of:
   (i) positioning a container on a pallet, wherein the container comprises a bottom wall and side walls extending circumferentially around the bottom wall to define a reservoir wherein the side walls have a circumferential inner edge defining a reservoir opening, wherein the container is positioned on the pallet exposing the reservoir opening,
   wherein the container includes a planar surface radially projecting outward from said circumferential inner edge; wherein the reservoir opening comprises a reservoir opening plane having a center longitudinal axis (Yc) extending along a length (L) of the reservoir opening plane between opposing circumferential inner edges and through a centroid of the reservoir opening plane;
   wherein a first depth (D1) between the bottom wall and the reservoir opening plane is measured orthogonal to the center longitudinal axis and 1/5 of the length (L)

from a first circumferential inner edge, and a second depth (D2) between the bottom wall and the reservoir opening plane is measured orthogonal to the center longitudinal axis and 4/5 of the length from the first circumferential inner edge such that the first depth (D1) is longer than the second depth (D2);

(ii) moving the pallet comprising the container on a conveyor belt to a filling station comprising a nozzle in fluid communication with a tank containing a perfume composition;

(iii) dispensing, at the filling station, the perfume composition through the reservoir opening into the reservoir of the container; and (iv) attaching a vapor impermeable substrate to the planar surface of the container containing the dispensed perfume composition.

2. The method according to claim 1, further comprising step (v) of attaching a porous membrane to the container across the reservoir opening.

3. The method according to claim 1, wherein the vapor impermeable substrate is a rupturable vapor impermeable substrate.

4. The method according to claim 3, wherein said rupturable vapor impermeable substrate is disposed between the porous membrane and the reservoir opening.

5. The method according to claim 1, wherein the conveyor belt is operated at a line speed of greater than or equal to 14 cycles per minute.

6. The method according to claim 1, wherein the conveyor belt is operated at a line speed of 14 to 20 cycles per minute.

7. The method according to claim 1, wherein the conveyor belt is operated at a line speed of 16 to 20 cycles per minute.

8. The method according to claim 1, wherein the conveyor belt is operated at a line speed of 18 to 20 cycles per minute.

9. The method according to claim 1, wherein step (iii) comprises filling the perfume composition to a total perfume fill volume ($V_{FILL}$) of 75% of a total internal reservoir volume ($V_r$) of the reservoir, where the total internal reservoir volume ($V_r$)=a Surface Area (SA) of the reservoir opening multiplied by an Average Depth (Avg. D.) of the reservoir.

10. The method according to claim 1, wherein step (iii) comprises filling the perfume composition to a total perfume fill volume ($V_{FILL}$) of 65% of a total internal reservoir volume ($V_r$) of the reservoir, where the total internal reservoir volume ($V_r$)=a Surface Area (SA) of the reservoir opening multiplied by an Average Depth (Avg. D.) of the reservoir.

11. The method according to claim 1, wherein a headspace between the reservoir opening plane and the perfume composition has a headspace volume of at least 25% of a total internal reservoir volume ($V_r$) of the reservoir, where the total internal reservoir volume ($V_r$)=a Surface Area (SA) of the reservoir opening multiplied by an Average Depth (Avg. D.) of the reservoir.

12. The method according to claim 1, wherein a headspace between the reservoir opening plane and the perfume composition has a headspace volume of at least 35% of a total internal reservoir volume ($V_r$) of the reservoir, where the total internal reservoir volume ($V_r$)=a Surface Area (SA) of the reservoir opening multiplied by an Average Depth (Avg. D.) of the reservoir.

13. The method according to claim 1, wherein a third depth (D3) between the bottom wall and the reservoir opening plane is measured orthogonal to the center longitudinal axis (Yc) and 3/5 of the length (L) such that the third depth (D3) is less than the first depth (D1) and greater than the second depth (D2) to define a sloped profile of the bottom wall.

14. The method according to claim 1, wherein a third depth (D3) between the bottom wall and the reservoir opening plane is measured orthogonal to the center longitudinal axis (Yc) and 3/5 of the length (L) such that the third depth (D3) is greater than the second depth (D2).

15. The method according to claim 1, wherein the side walls include a first side wall and a second side wall opposing each other, wherein the first side wall is directly adjacent to said first circumferential inner edge and the second side wall is directly adjacent to a second circumferential inner edge, wherein the center longitudinal axis (Yc) intersects the first circumferential inner edge and the second circumferential inner edge wherein a height of the first side wall is measured orthogonal to an intersection of the center longitudinal axis and the first inner circumferential edge and a height of the second side wall is measured orthogonal to an intersection of the center longitudinal axis and the second inner circumferential edge, wherein the height of the first side wall is longer than the height of the second side wall.

16. The method according to claim 1, comprising a total perfume fill volume ($V_{FILL}$) of from about 4 ml to 30 ml.

17. The method according to claim 1, comprising a total perfume fill volume ($V_{FILL}$) of from about 6 ml to 20 ml.

* * * * *